(12) United States Patent
Kothe et al.

(10) Patent No.: US 7,041,798 B1
(45) Date of Patent: May 9, 2006

(54) METHOD FOR THE CHROMATOGRAPHIC FRACTIONATION OF PLASMA OR SERUM, PREPARATIONS, SO OBTAINED, AND THEIR USE

(75) Inventors: Norbert Kothe, Kronberg/Taunus (DE); Dieter Rudnick, Dreieich (DE); Michael Kloft, Darmstadt (DE)

(73) Assignee: Biotest Pharma GmbH, Dreieich (DE)

( * ) Notice: Subject to any disclaimer, the term of this patent is extended or adjusted under 35 U.S.C. 154(b) by 181 days.

(21) Appl. No.: 10/030,801

(22) PCT Filed: Jun. 23, 2000

(86) PCT No.: PCT/EP00/05827

§ 371 (c)(1),
(2), (4) Date: Jun. 14, 2002

(87) PCT Pub. No.: WO01/05809

PCT Pub. Date: Jan. 25, 2001

(30) Foreign Application Priority Data

Jul. 14, 1999 (DE) ................. 199 32 782

(51) Int. Cl.
*A61K 39/395* (2006.01)
*C07K 1/20* (2006.01)

(52) U.S. Cl. ............. 530/364; 424/176.1; 424/177.1; 530/390.1; 530/390.5; 530/415

(58) Field of Classification Search ........ 530/364, 530/390.1, 390.5, 415; 424/176.1, 177.1
See application file for complete search history.

(56) References Cited

U.S. PATENT DOCUMENTS 5,429,746 A    7/1995    Shadle et al.

FOREIGN PATENT DOCUMENTS

| EP | 0 339 919 A | 11/1989 |
| EP | 0 717 049 A | 6/1996 |

OTHER PUBLICATIONS

Goheen et al, Jour. of Chromatography, 326, 235-241, 1985.*
Goudswaard et al, Immunochemistry, 14, 717-719, 1977.*
Hirkal Z. et al; "Hydrophobic interaction chromatography of serum proteins or phenyl sepharose CL-4B"; Journal of Chromatography, vol. 242, No. 2 (1982); pp. 385-388.

* cited by examiner

*Primary Examiner*—David Saunders
(74) *Attorney, Agent, or Firm*—Norris McLaughlin & Marcus, P.A.

(57) ABSTRACT

The invention relates to the fractionation of plasma or serum into at least one albumin fraction and one immunoglobulin fraction by hydrophobic interaction chromatography. The fractionation is carried out using an incremental salt gradient, especially an ammonium sulfate buffer. The invention also relates to preparations obtained by using said method and to their use.

23 Claims, 6 Drawing Sheets

Figure 1:
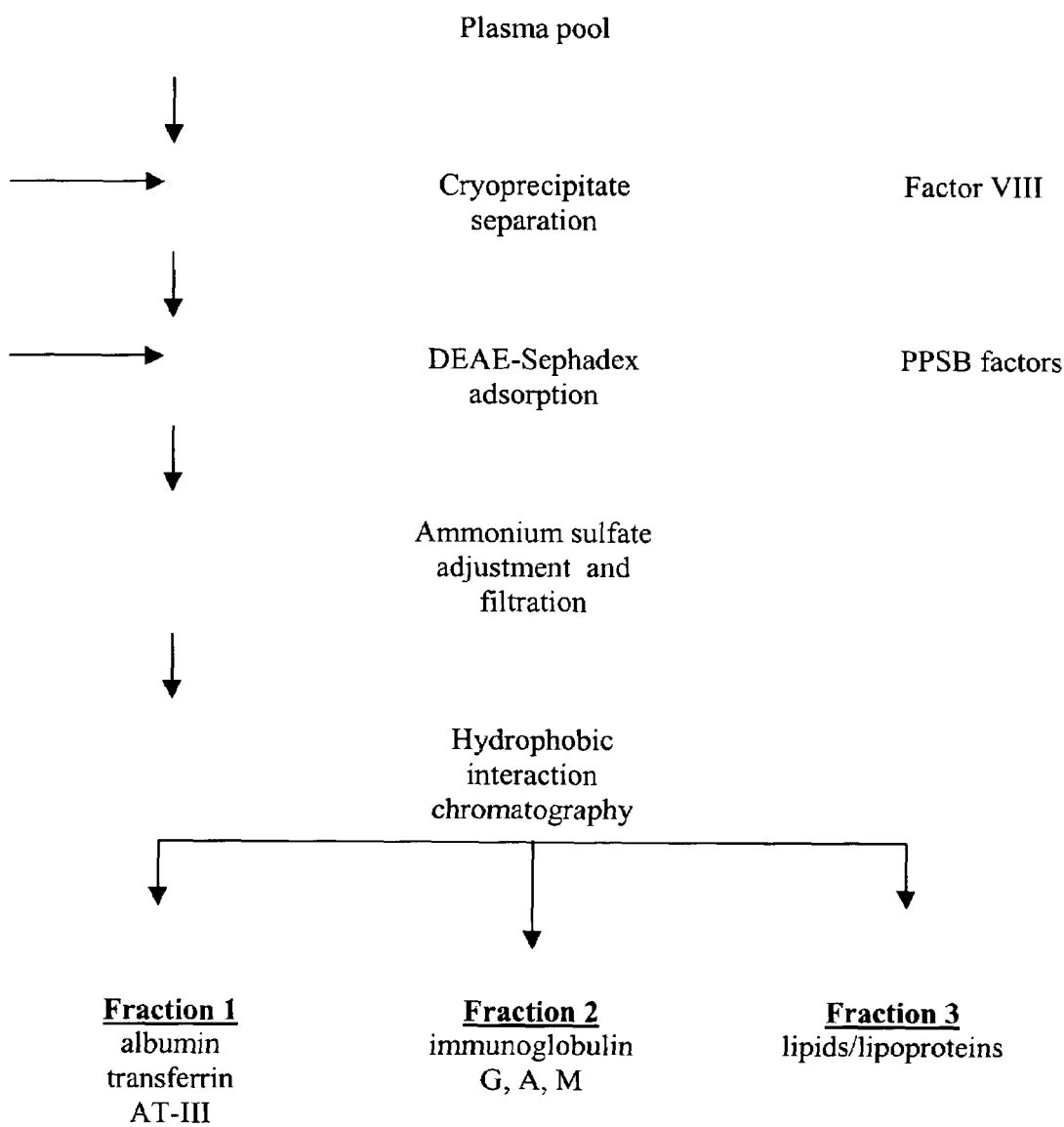

HPSE CHROMATOGRAM OF AN IMMUNOGLOBULIN G SOLUTION, PREPARED ACCORDING TO EXAMPLE 8

HPSE CHROMATOGRAM OF AN ANTITHROMBIN (AT-III) SOLUTION, PRODUCED BY EXAMPLE 8

RESULT:

| # | RET TIME (min) | AREA (uV*sec) | % AREA | NAME |
|---|---|---|---|---|
| 1 | 15.967 | 16341442 | 98.35 | |
| 2 | 21.717 | 274834 | 1.65 | |

METHOD FOR THE CHROMATOGRAPHIC FRACTIONATION OF PLASMA OR SERUM, PREPARATIONS, SO OBTAINED, AND THEIR USE

This application is a 371 of PCT/EP00/05827 filed on Jun. 23, 2000.

The invention relates to a method, described in the claims, for the chromatographic fractionation of plasma or serum, especially of human plasma and/or serum, at a hydrophobic interaction phase by means of a stepwise salt gradient, as well as to the protein preparations, prepared therefrom, and their use.

The first attempts to fractionate human plasma industrially were carried out already in the 1940s. The methods used are based on the precipitation of protein fractions by means of alcohol, different plasma proteins being obtained in an enriched form by varying the pH, the ionic strength, the temperature and the alcohol concentrations in these fractions.

The fractions, which are obtained by this process and contain immunoglobulins and albumin, are of particular importance for the therapeutic application. An overview of the above-mentioned methods is given in the review articles (J. E. More and M. J. Harvey, Blood Separation and Plasma Fractionation, Wiley-Liss, New York, 1991, 261–306, and P. Kistler and H. Friedl, Methods of Plasma Protein Fractionation, Academic Press, London, 1980, pages 3 to 15).

Aside from alcohol, other precipitating reagents, such as ammonium sulfate and polyethylene glycol, are used to recover plasma fractions (A. P. Phillips, K. L. Martin and W. H. Horton, The choice of methods for immunoglobulin IgG purification. Yield and Purity of Antibody Activity. J. of Immunological Methods, 74 (1984) 385–393. A. Polson et al., The Fractionation of Protein Mixtures by Linear Polymers of High Molecular Weight. Biochem. Biophys. Acta, 82 (1964) 463– 475; P. D. Gorevich et al., Methods of Enzymology, vol. 116, 1985, 3–25; DE 2936047C2).

In principle, all precipitation methods for isolating plasma proteins have some disadvantages. The reagents, used for the precipitation, bring about a partial denaturation of the separated proteins. This can be seen by the formation of aggregates and the incompatibilities associated therewith during the therapeutic application. Further expensive cleaning steps are required in order to obtain compatible preparations from the protein fractions so obtained.

A further disadvantage of the methods consists therein that precipitation reactions, especially in the case of mixtures as complex as human plasma, are never quantitative. This and the additional cleaning steps required lead to appreciable losses in yield.

These methods therefore do not represent an optimum utilization of the valuable starting material, particularly of human plasma or human serum.

For this reason, attempts were made to carry out the plasma fractionation with gentler methods and higher yields. For this purpose, adsorptive methods are available.

Special properties of proteins, such as charge, hydrophobicity, size and characteristic binding properties are utilized to bind the proteins to suitable ligands. It is particularly advantageous if these ligands are bound to a water-insoluble, stationary carrier. The binding of the proteins to the substituted carrier can be carried out in batch methods or as a column chromatographic method, the latter having proved to be particularly advantageous. Anionic and cationic exchangers, affinity and hydrophobic phases, as well as exclusion chromatographic materials were used for the chromatographic isolation of plasma proteins.

These chromatographic methods were previously used primarily for the fine purification of precipitated plasma fractions.

Some examples are listed in the following.

In the EP 0447585B1, the isolation of immunoglobulin G from Cohn Paste II is described.

The EP 0352500B1 discloses the production of immunoglobulin M from Paste III, which has been precipitated with alcohol.

Transferrin (DE 3733181C1, $\alpha_1$-antitrypsin (EP 0717049A1, U.S. Pat. No. 5,610,285) and antithrombin III (EP 0844254A2) can be isolated from Cohn Paste IV with the help of different chromatographic methods.

Cohn Paste V is the starting material for the, the chromatographic preparation of albumin (EP 0792887A1) as well as for purifying $\alpha_1$ acidic glycoprotein (U.S. Pat. No. 5,739,293).

Likewise, alcohol containing supernatant solutions of the Cohn fractionation can be used as starting material for a chromatographic preparation of albumin (EP 04022058B1).

A combination of alcohol precipitation and chromatography for obtaining plasma proteins is disclosed in U.S. Pat. No. 5,138,034.

The direct recovery of immunoglobulin G and albumin from human plasma, by means of ion exchange chromatography without a prior precipitation and separation of a precipitate is described in the DE 3640513C2 and the WO 94/29334.

A survey of the use of chromatographic methods for recovering proteins from human plasma may be found in J. M. Curling, Separation of Plasma Proteins, Pharmacia Fine Chemicals AB, Uppsala, Sweden, 1993.

As already mentioned above, all the methods described have significant disadvantages. For example, all plasma proteins, obtained by precipitation reactions, lead to considerable losses in yield and require additional, expensive purification steps, in order to make the therapeutic application possible. In addition, a great technical effort is required for cooling the reaction vessels, centrifuges or filters.

The products, obtained by means of ion exchange chromatography from plasma, require expensive pre-working up of the human plasma.

For carrying out the ion exchange chromatography, the plasma must be adjusted to do a defined, low ionic strength. This can be achieved by diluting or re-buffering.

Large volumes result here, which limit the amount of plasma, which can be processed on an industrial scale. Moreover, the fibrinogen, contained in the human plasma, must be removed by an additional step before the chromatography, in order to prevent blockage of the column.

S. Goheen et al., in the J. of Chromatography, 326 (1985), 235–241, describe a method for fractionating human serum. For this purpose, a Bio-Gel TSK Phenyl-5PW column is charged with the starting solution and subsequently eluted at 0° C. by means of a linear ammonium sulfate gradient in 0.1M sodium phosphate buffer. Such a linear elution can be carried out only on an analytical scale, since otherwise, when charging the starting solution and using said initial concentration of 1.7M, the column would become blocked if one were to work on a preparative scale. Moreover, it is necessary to work at 0° C., in order to improve the resolution of the chromatogram. Because of the technical effort involved, such a procedure cannot be transferred to a process on a preparative scale.

It is an object of the invention to provide to a method, which can be carried out economically on an industrial scale, for the fractionation of plasma, especially of human plasma, or of serum, especially of human serum, which furnishes native, unmodified plasma proteins in high yield. For this method, precipitating and dissolving therapeutically relevant proteins shall be largely avoided and the process shall take place at room temperature.

Pursuant to the invention, this objective is accomplished owing to the fact that plasma or serum, especially of human origin, preferably a plasma or serum, which has been freed from the clotting factor VIII and/or the clotting factors of the PPSB complex, especially of human origin, is chromatographed at a hydrophobic phase using a stepwise salt gradient. Especially ammonium sulfate is suitable as salt.

Surprisingly, it has been found that, with the help of the hydrophobic interaction chromatography, plasma or serum can be separated at least into an immunoglobulin-containing fraction and an albumin-containing fraction on a preparative scale and that the chromatography can be carried out at room temperature without the use of expensive cooling equipment.

The inventive method is described in greater detail in the following.

1. Fractionation

Pursuant to the invention, (human) plasma or (human) serum can be used, which may be freed from clotting factors. Moreover, animal plasma or serum with or especially without clotting factors can also be used. The starting material can be obtained from a normal donor pool as well as from selected donors with high antibody titers against viral, bacterial or cellular antigens. In the case of selected starting materials (hyperimmunoglobulin), preferably those with high titers against CMV, hepatitis B, chickenpox, tetanus or anti-D are selected.

As starting material for the inventive method, preferably a plasma, particularly a human plasma or human serum, which has been freed from clotting factors, is used. The separation of the valuable clotting factors from plasma, which themselves are of great therapeutic benefit, is known.

For example, the cryo-precipitate, which has been obtained from a thawing process, is used as starting material for the preparation of factor VIII concentrates and the factors II, VII, IX and X (PPSB complex) are isolated by adsorption on an ion exchanger and, in purified form, are also used therapeutically.

Therefore, for obtaining the preferred starting material for the inventive method, a plasma, especially one obtained according to the guidelines of the blood donor system by means of plasmapheresis, can be thawed at +4° C. and the cryo-precipitate removed by centrifugation. Factor VIII can be produced from this. The clotting factors of PPSB complex are separated by adsorption on an ion exchanger, such as a cross-linked to dextran, substituted with diethylaminoethyl groups (such as DEAE Sephadex® A50).

Preferably, sufficient gradient salt per liter, solid ammonium sulfate in the case of ammonium sulfate, is added to the starting material, with or without clotting factors, so that, after several hours of stirring at room temperature, such as 3 to 20 hours, and, optionally, after the addition of water for injection purposes, the salt solution, especially the ammonium sulfate solution, has a conductivity, which corresponds to the starting concentration of salt, especially of ammonium sulfate, selected for the commencement of the chromatography. After the addition of 0.5 to 5% filter aid, such as standard Super Cell or a different filter aid such as perlite, harbolite or celite, the solution is filtered. The filtrate is used as the starting solution for the chromatography. The hydrophobic interaction phase preferably is equilibrated to the desired initial concentration of salt, especially of ammonium sulfate corresponding to the concentration selected in the starting solution.

The chromatographic separation is based on the interaction of hydrophobic domains of the proteins molecules with hydrophobic groups on the stationary chromatographic phase. Under physiological conditions, the hydrophobic groups of the proteins molecules are not freely accessible, so that binding to a hydrophobic interaction phase does not take place. By adding the salt, especially ammonium sulfate, the hydrate sheath of the proteins is decreased, so that the hydrophobic domains are available for a hydrophobic interaction.

The hydrophobicity of the stationary phase is selected pursuant to the invention so that an interaction of certain proteins with the phase can take place. The binding to the phase depends, on the one hand, on the hydrophobicity of the chromatographic matrix and, on the other, on the salt concentration and especially the ammonium sulfate concentration of the solution. Since precipitation of the proteins takes place at a high salt concentration and especially at a high ammonium sulfate concentrations, the salt concentration, such as the ammonium sulfate concentration, is selected according to the hydrophobicity of the chromatographic phase, so that the desired interactions take place at a salt concentration or an ammonium sulfate concentration, which predominantly does not lead to precipitation.

This is shown, for example, in Table 1, in which the proportion of proteins, still in solution, is given as a function of the concentration of ammonium sulfate. Satisfactory values are not obtained at values of 1.4 moles/L of ammonium sulfate and above.

Accordingly, the concentration of salt, especially of ammonium sulfate, should be less than 1.4 moles/L.

Accordingly, for the effective separation of immunoglobulin and albumin fractions, the initial concentration of ammonium sulfate is less than 1.4 moles/L, to which, if desired, the chromatography phase and the starting solution are adjusted, washing is carried out preferably with a buffer of this salt concentration and the ammonium sulfate concentration subsequently is lowered.

Preferably, the separation is carried out if the high concentration is 0.6 to less than 1.4 moles/L, particularly if it is 1.3 moles/L, more particularly if it is 0.6 to 1.2 moles/L, especially if it is 0.7 to 1 mole/L and most particularly if it is 0.8 to 0.9 moles/L, and if the lowered concentration is 0.4 to 0 moles/L and especially 0.3 to 0 moles/L.

With such a concentration gradient, initially an albumin-containing fraction and then an immunoglobulin-containing fraction is obtained. The latter may still contain lipids, which advantageously are removed. For this purpose, a further concentration step of the ammonium sulfate can be used in the second step. Such a concentration step starts, for example, at 0.4, especially 0.3 moles/L to 0.1 moles/L, particularly 0.3 moles/L to 0.1 moles/L, more particularly 0.3 to 0.15 moles/L and most particularly 0.3 moles/L and the concentration during this step subsequently is lowered to below 0.1 moles/L to 0 moles/L. The lipids are removed from the phase only at the lowest, optionally zero (0 moles/L) concentration and with that, are removed from the immunoglobulin fraction, which leaves the phase at higher ammonium sulfate concentrations.

The chromatography is carried out under the usual conditions, known for such phases, such as a pH of, for example, 7.0 and sodium (hydrogen) phosphate buffer or trishydroxymethylaminomethane as eluant. Phosphate buffers (such as 0.01 M $NaH_2PO_4$) are particularly preferred.

For the inventive process, the known materials are suitable as hydrophobic interaction phases. These include phenyl-substituted or alkyl-substituted phases based on copolymers of glycidyl methacrylate and ethylene glycol dimethacrylate, copolymers of polystyrene and divinylbenzene or silica gel coated with dextran or silica gel.

Alkyl-substituted and, particularly, phenyl-substituted copolymers of glycidyl methacrylate and ethylene glycol dimethacrylate are especially suitable.

These are commercially available under the trade names of TSK-Phenyl 5PW® and Toyopearl-Phenyl 650®.

Pursuant to the invention, an initial ammonium sulfate concentration of, for example, 0.7 to 1.0 moles/L, preferably of 0.8 to 1.0 moles/L and particularly of 0.9 moles/L is selected for the chromatographic separation.

As is evident from Table 2, particularly good results are obtained at such concentrations for the chromatographic separation on TSK-Phenyl SPW®.

As described above, the starting solution, adjusted to an ammonium sulfate concentration of 0.9 moles/L, can be applied on the equilibrated hydrophobic chromatography phase. At this salt concentration, a fraction 1 is obtained, which passes through the phase without being bound. The bound proteins are eluted with 0.01 moles/L of sodium phosphate of pH 7.0 from the phase as fraction 2, that is, the ammonium sulfate concentration is reduced to here 0 moles/L.

The composition of the chromatographic fractions obtained is shown in Table 3. As can be seen, a fraction 1 is obtained, which is referred to as the albumin fraction and is very similar in composition to a supernatant II/III of the alcohol fractionation of Cohn. It contains the important proteins, namely albumin, transferrin, antithrombin III and α-antitrypsin. All immunoglobulins are contained almost quantitatively in fraction 2, which therefore is similar to the composition of a paste II/III obtained by the cold ethanol method.

As can furthermore seen from Table 3, lipids and lipoproteins are also contained in fraction 2. These can make it more difficult to process fraction 2 into therapeutically usable proteins solutions, so that it has proven advantageous to integrate a further elution step in the process to obtain a third fraction. For this purpose, after fraction 1 is obtained, one can start at the highest concentration, such as 0.9 moles/L of ammonium sulfate and then continue working with a step gradient. For example, fraction 2 can be isolated at 0.3 moles/L.

The protein composition of this immunoglobulin-containing Fraction 2 does not differ format of the fraction described above (Table 3, Fraction 2), with the exception that the lipoprotein content is less than 5%.

The lipoprotein fraction remains bound to the chromatography phase at 0.3 moles/L and higher ammonium sulfate concentrations and can be eluted from the phase with 0.01 moles/L of sodium phosphate at pH 7.0 as Fraction 3. In other words, the ammonium sulfate concentration is reduced here to 0 moles/L.

Preferably, therefore, 3 fractions are separated during the inventive, hydrophobic interaction chromatography, namely initially the albumin fraction, then the immunoglobulin fraction and then the lipoprotein fraction.

The inventive process is shown diagrammatically in FIG. 1.

2. Recycling

Figure 2:
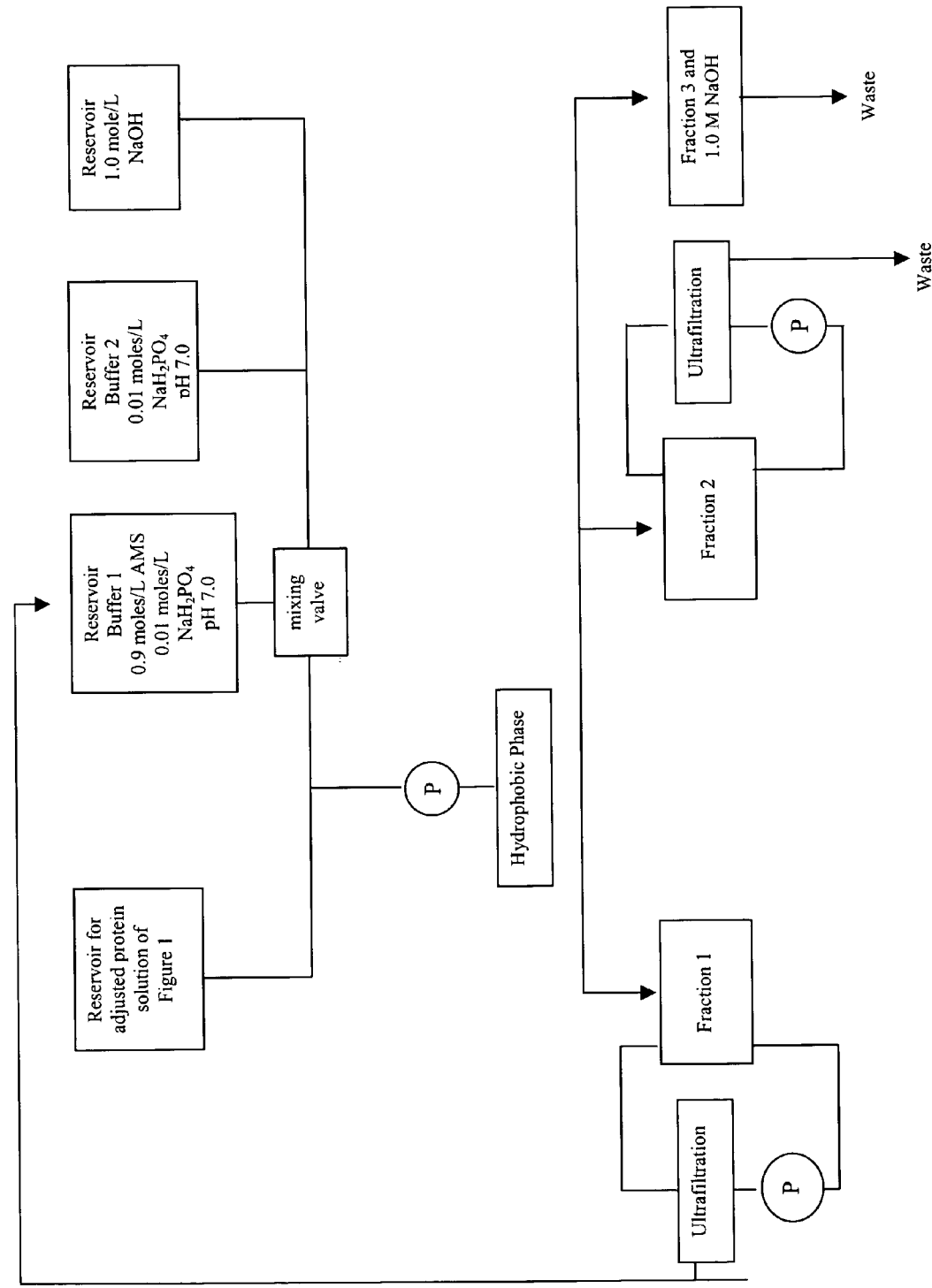

Buffer solutions, containing buffer salt, such as ammonium sulfate, are required in appreciable amounts for the industrial scale application of the method. In order to minimize the consumption of this salt as much as possible, a recycling method, which is shown in FIG. 2, is used pursuant to the invention.

For this method, the ammonium sulfate buffer 1, for example, which has been adjusted to the desired (high) concentration, can be recycled as permeate from the first fraction obtained, for example, by means of suitable ultrafiltration membranes, while the first fraction is being collected and concentrated continuously. For the purpose of separating the second and, optionally the third fraction, a buffer with the respectively desired concentration is then lowered, as stated pursuant to the invention, by mixing the ammonium sulfate buffer 1 with a salt, which is not a salt gradient, that is, with a salt other than the ammonium sulfate buffer 2, or by using only the buffer 2, and the second or third fraction is separated, depending, on the number of fractions desired.

Preferably, as described above, three fractions are produced by using a step gradient after separating Fraction 1, the ammonium sulfate concentrations, given above, being selected.

The fractions can be concentrated continuously, for example, by means of ultrafiltration.

Preferably furthermore, the chromatographic phase is purified after each cycle with sodium hydroxide solution from a reservoir 3, sterilization taking place at the same time.

For example, after the column is charged with the plasma protein solution, which has been adjusted to a buffer 1 and filtered, for obtaining Fraction 1, it is washed with buffer 1 (for example, 0.9 moles/L of ammonium sulfate, 0.01 moles/L of $NaH_2PO_4$ of pH 7.0), in order to obtain all of Fraction 1. The fraction, so obtained, is collected and concentrated continuously using an ultrafiltration unit with a cut-off of 10 KD. The permeate, obtained here, is returned to the reservoir for buffer 1.

To elute Fraction 2, the salt concentration or ammonium sulfate concentration is reduced as indicated and, for example, a mixed buffer can be produced or a buffer 2, which does not contain any salt, such as ammonium sulfate, is selected alone, depending on how many separation steps are desired.

For a step gradient, for example, for eluting Fraction 2, buffer 1 (0.9 moles/L of ammonium sulfate, 0.01 moles/L of $NaH_2PO_4$, pH 7.0) and buffer 2 (0.01 moles/L of $NaH_2PO_4$, pH 7.0) can be mixed on-line in a ratio of, for example, 1:3. This mixing ratio results in an elution buffer for Fraction 2 with the mixed concentration of, for example, 0.3 moles/L of ammonium sulfate, 0.01 moles/L of $NaH_2PO_4$, pH 7.0. The collected Fraction 2 is also concentrated on-line using an ultrafiltration unit with a cut-off of 10–30 KD.

The lipoproteins are then eluted from the hydrophobic phase with buffer 2 (0.01 moles/L of $NaH_2PO_4$, pH 7.0) and discarded.

This method can be varied by changing the buffer/salt concentrations and mixing ratios within the inventively deserved range and the usual conditions known to those skilled in the art for said chromatography phases. For example, a 1.1 to 1.5 etc. mixture can be produced from a buffer 2 with a concentration of 1 mole/L.

When larger amounts are processed, several chromatographic cycles are carried out. Preferably, the hydrophobic phase is therefore cleaned and, at the same time, sterilized with 1.0 moles/L of sodium hydroxide after each separation cycle. The sodium hydroxide solution is in reservoir 3.

3. Further Processing

Fractions 1 and 2, obtained from the hydrophobic phase using the inventive method, can be processed further into therapeutically usable, plasma protein solutions of high purity by known methods, such as those described in the publications mentioned above. Such preparations are used for respective deficiency or disease states. For example, in the case of infections preparations, which were prepared pursuant to the invention from selected starting material, such as those containing, anti-CMV or anti-HBs, anti-chickenpox, tetanus or anti-D, such preparations can be administered for the appropriate infection.

Amounts and forms of administration are known here. For example, the preparations may be administered as injections or i.m. injection or i.v. infusion. In addition to the active ingredient, the pharmaceutical composition may also contain the known inactive ingredients, which include, for example, electrolytes, amino acids or sugars.

a) Immunoglobulin G

Figure 3:
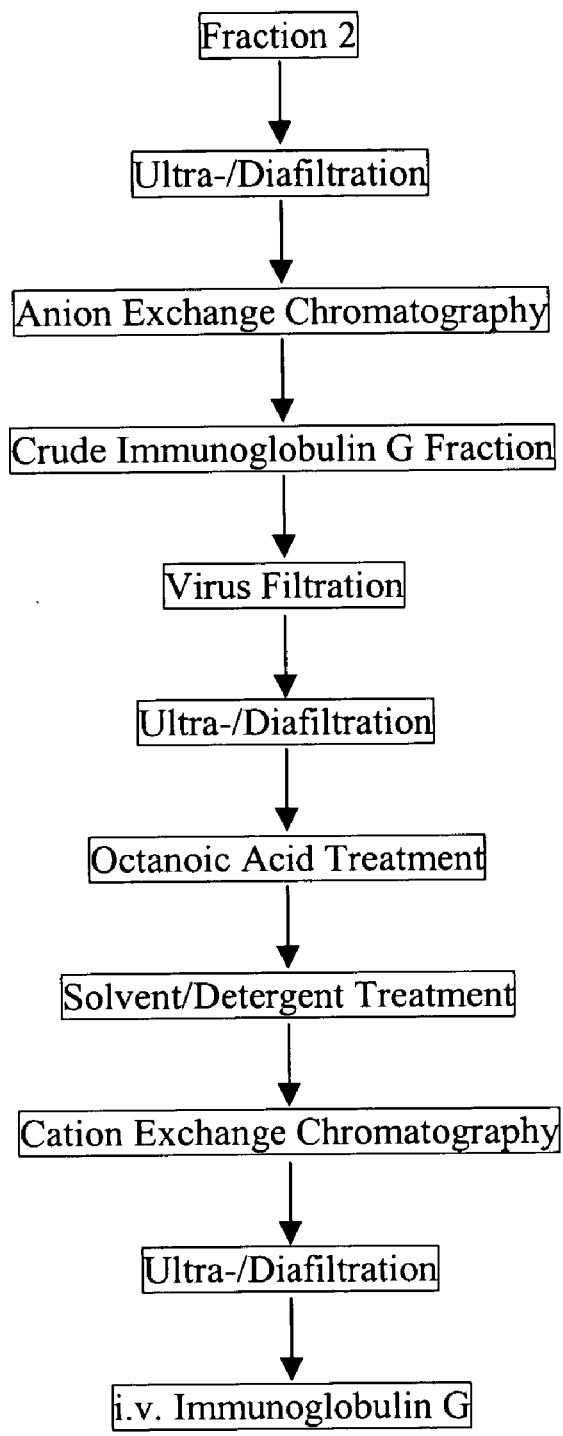

For example, especially an immunoglobulin G, one which is i.v. compatible, can be produced from the immunoglobulin fraction (Fraction 2). For this purpose, known methods, such as those already described in DE 3640513C2 as well as EP-B 447 585, can be employed. This procedure is shown in FIG. 3 and comprises, essentially, anion exchange chromatography, optionally virus filtration, treatment with octanoic acid, cation exchange chromatography and the usual concentrating, filtering and sterilizing steps.

For example, by means of diafiltration, the concentrated Fraction 2 from the hydrophobic interaction chromatography can be re-buffered to 0.05 to 0.10 moles/L of $NaH_2PO_4$ having a pH of 6.5 and preferably to 0.06 moles/L of $NaH_2PO_4$, having a pH of 6.5.

For working it up further, this solution is subjected to an anion exchange chromatography. For this purpose, the anion exchanger is equilibrated with 0.01 to 0.05 moles/L of $NaH_2PO_4$ of pH 6.5 and preferably with 0.03 moles/L of $NaH_2PO_4$ having a pH of 6.5, and the diafiltered protein solution is diluted with water for injection purposes (WFI), so that the salt concentration here also is 0.01 to 0.05 moles/L of $NaH_2PO_4$ at a pH of 6.5 and preferably 0.03 moles/L of $NaH_2PO_4$ at a pH of 6.5. Under these conditions, a crude immunoglobulin G fraction passes through the column without being bound, while all other proteins bind to the chromatographic phase.

The bound proteins are eluted with a buffer of high salt concentration (0.02 moles/L of $NaH_2PO_4$, 1.0 moles/L of NaCl, at a pH of 6.5).

The crude immunoglobulin G fraction optionally is filtered through a virus filter, concentrated by means of ultrafiltration or diafiltration and re-buffered to 0.01 to 0.05 moles/L of sodium acetate of pH 5.5 and preferably to 0.02 moles/L of sodium acetate of pH 5.5.

This adjusted crude fraction consists to the extent of more than 99% of immunoglobulin G. However, it is contaminated with proteolytic enzymes.

These can be removed with octanoic acid by the method of EP 0447585B1. For this purpose, the conditioned solution is treated with 0.4 to 1.5% by volume and preferably 0.8 to 1.0% by volume and especially with 0.8% by volume of octanoic acid and filtered with addition of calcium chloride. Subsequently, viruses are inactivated with 0.3% of tri-n-butyl phosphate and 1% of Tween 80. At the conclusion of the reaction time, the solution is adjusted with water for injection purposes to a conductivity of 0.02 moles/L of sodium acetate, pH 5.0 buffer.

The reagents of the octanoic acid treatment and of the virus inactivation, as well as the IgG aggregates, contained in the solution, are removed by chromatography on a cationic exchanger. For this purpose, the adjusted immunoglobulin G solution is added to the equilibrated cationic exchange column and washed with 0.02 moles/L of sodium acetate at a pH of 5.0 and the immunoglobulin G fraction is eluted with a buffer, consisting of 0.02 moles/L of sodium acetate, 0.3 moles/L of sodium chloride, and a pH of 5.0. The column is purified with 0.02 moles/L of sodium acetate, 1.0 moles/L of sodium chloride, having a pH of 5.0, and 1.0 moles/L of sodium hydroxide.

The immunoglobulin G fraction is diafiltered against 0.3 moles/L of glycine of pH 5.0 and concentrated to a protein concentration of 50 g/L.

The i.v. compatible IgG preparation of high purity can also be worked up analogously by other known methods.

The intravenously compatible immunoglobulin G preparations, so produced, have some advantages over the conventional solutions, which usually are obtained by precipitations from plasma. For example, the IgG sub-class composition corresponds to the natural distribution, which occurs in plasma. The IgA content is less than 0.15% and the IgM content less than 0.02% of the total protein content. The proportion of IgG aggregates is less than 0.25%. Possible impurities, which can lead to incompatibility reactions, such as pre-kallikrein activator, pre-kallikrein, kallikrein, kininogens, plasmin, plasminogen and factor XI cannot be detected. All other analytical parameters correspond to the European Pharmacopoeia for i.v. immunoglobulin G preparations.

Accordingly, the preparation, so obtained, fulfills all criteria and differs from the known product, on the one hand, by the higher IgG proportion and, on the other, with respect to the sub-class composition.

b) Albumin, Antithrombin III Transferrin

Antithrombin III (AT-III), transferrin and albumin, for example, can be obtained from the inventively produced Fraction 1.

Figure 4:
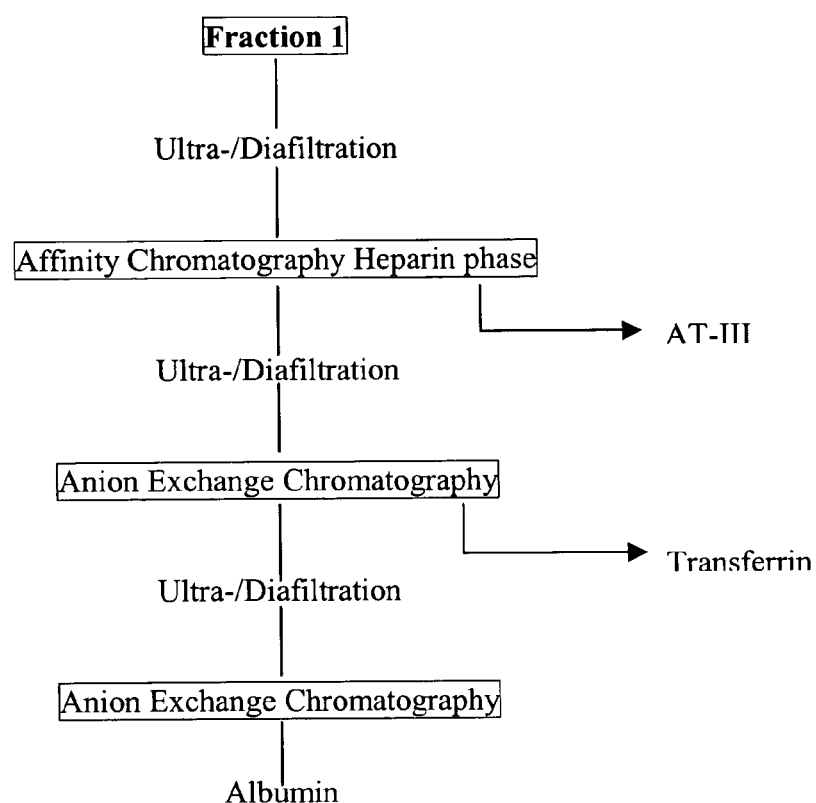

A corresponding method is shown in FIG. 4 and comprises essentially affinity chromatography, anion exchanges chromatography, virus inactivation and conventional filtering, concentrating and sterilizing steps.

Accordingly, antithrombin III can be obtained from the starting materials containing it, namely the ultrafiltered and diafiltered Fraction 1 by means of affinity chromatography on a heparin carrier. Such a procedure is described in the EP-A 844 254 as a preliminary cleaning step for obtaining antithrombin III, which is freed from impurities, a heat treatment and/or a metal chelation treatment being carried out subsequently there. In the inventive method, the affinity chromatography can accordingly also be carried out. A salt solution of low concentration, such as 0.1 to 0.2 moles/L sodium chloride solution, leads to the binding of antithrombin III and a higher salt concentration, such as 1.0 to 2.0 moles/L sodium chloride solution leads to elution. Fraction 1 can thus be adjusted to a buffer medium of 0.02 moles/L of $NaH_2PO_4$, 0.150 moles/L sodium chloride solution and a pH of 7.0 and applied to the affinity phase.

Albumin and transferrin pass through the column without being bound. The column is washed with 0.02 moles/L of $NaH_2PO_4$ and 0.4 moles/L of NaCl at a pH of 7.0. Subsequently, the AT-III, bound to the heparin carrier, is eluted with 0.02 moles/L of $NaH_2PO_4$ and 2.0 moles/L of NaCl at a pH of 7.0. The AT-III solution obtained is re-buffered to physiological conditions and can be processed further to a therapeutically usable preparation by known methods, such as virus filtration and pasteurization.

The fraction, passing through the affinity chromatography column and containing albumin and transferrin, can be separated into transferrin by the method of DE 3733181C1 and albumin according to the method of EP 0402205B1 or EP 0792887A1. For example, after re-buffering the above-mentioned run-through filtration of the affinity chromatography to 0.02 moles/L of tris and 0.030 moles/L of sodium chloride at a pH of 7.0, the solution can be applied to an anion exchanger. The transferrin is collected as a run-through fraction and virus-inactivated by known methods and processed further. The albumin fraction, subsequently eluted from the anion exchanger with 0.02 moles/L of tris and 1.0 moles/L of sodium chloride at a pH of 7.0, can be adjusted, for example, to a conductivity of 1.8 mS/cm with a sodium acetate buffer pH of 6.0 and subjected once again to anion exchange chromatography. Any traces of transferrin present are removed by changing the pH to a value of 5.2. The albumin is eluted from the anion exchanger at a pH of 4.5 and a conductivity of 1.8 mS/cm. The product is processed further to a therapeutically usable albumin preparation by known methods.

Known materials are used for all the chromatographic steps employed in the above-mentioned methods. As cation exchanger, for example, CM-Accell®, SP-Spherodex®, SP-Trisacryl-LS® or Fraktogel-TSK-SP 650®, Poros HS® or S-HyperDF® or SOURCE-305®, CM HyperDF® can be used and the salt concentration adjusted correspondingly. As anion exchanger, for example, QMA-Accell®, DEAE-Spherosil® or DEAE-Sepharose®, Poros HQ®, Q-HyperDF® and SOURCE-30Q® can be used. Further suitable materials are CM-Accell®, SP-Spherodex-M® or phases, produced on the basis of synthetic polymers, such as SP-Trisacryl-LS® and CM-Trisacryl-LS®. For example, heparin-Sepharose® or heparin-immobilized synthetic polymers, such as Toyopearl AF-Heparin 650M® can be used for the affinity chromatography and the above-mentioned compositions can also be selected as buffers.

Preferably, chromatographic media based on synthetic polymers, such as those commercially obtainable under the trade names of Poros®, SOURCE®, Macroprep®, TSK®, Toyopearl® and Hyper D®, are used in the inventive method. Said phases, substituted as anion exchangers, cation exchangers, hydrophobic interaction matrix and affinity matrix, are available. Tertiary or quaternary amino groups form anion exchanges, sulfoalkyl groups or carboxyalkyl groups form cation exchangers, and substituents, such as alkyl or phenyl or heparin groups, form hydrophobic phases or affinity matrices. The appropriate buffer media and elution conditions for these are known to those skilled in the art.

Because of the relative resistance to pressure, high flow rates are possible even if the particle size is small. With that, the processes described can be carried out economically in a short time and with a high throughput. Moreover, the chromatographic phases offer the advantage that they are chemically inert to sterilizing reagents and therefore particularly suitable for the production of pharmaceutical products.

For the sterilization, treatments with beta-propiolactone, TNBP/Tween, TNBP/NaCholate, TNBP, optionally in combination with UV radiation or virus filtration, can be employed. The filters used, such as Planova®, Virosolv® and UltriporDD50®, are known.

The products, produced pursuant to the invention in this manner, can be stored in liquid or lyophilized form.

The advantage of the inventive method lies therein that said starting materials can be purified rapidly and easily so that the pure products obtained can be obtained without significant losses in yield and correspond essentially to their natural composition.

The invention is explained by the following examples.

EXAMPLE 1

As starting material, 5.4 L of a human plasma, freed from clotting factors, is used. The clotting factors are removed by known methods by separation of the cryo-precipitate and by absorption of the PPSB factors at DEAE-Sephadex-A50®.

Ammonium sulfate (1.2 moles/kg) is added to this pre-treated plasma, which is then stirred for 5 hours at room temperature, after which water for injection purposes (WFI) is added until the conductivity reaches a value of 112 mS/cm (20° C.), which corresponds to the conductivity of a 0.9 molar ammonium sulfate solution, and stirring is continued for 6 to 12 hours. After addition of 2% (w/w) of filter aid (such as standard Super Cell), stirring is continued for 1 hour, after which the solution is clarified over a depth-filter, such as a Seitz Supra 80P.

A steel column (373 mL), filled with TSK-Phenyl 5PW® is equilibrated with 0.9 moles/L of ammonium sulfate and 0.01 moles/L of $NaH_2PO_4$ having a pH of 7.0. The prepared and filtered plasma solution is applied in portions of 370 mL at a flow rate of 70 mL/min. At the end of the application, the column is washed with five column volumes of the equilibrating buffer and this fraction is collected (Fraction 1). During the collection of Fraction 1, an ultrafiltration on a 10 KD membrane, such as Omega®, Pall-Filtron is carried out at the same time, the permeate being recycled to the reservoir for the equilibrating buffer.

After that, Fraction 2 is obtained with an elution buffer, consisting of 0.3 moles/L of ammonium sulfate and 0.01 moles/L of $NaH_2PO_4$ at a pH of 7.0 and employed in an amount of four times the capacity of the column. The elution buffer is prepared from the equilibration buffer (0.9 moles/IL of ammonium sulfate and 0.01 moles/L of $NaH_2PO_4$ having a pH of 7.0) and a 0.01 moles/L solution of $NaH_2PO_4$ having a pH of 7.0, using a mixing valve. For this purpose, the two buffers are mixed on-line in a ratio of 1:3.

The lipoprotein fraction (Fraction 3) is dissolved from the column by adding 3 volumes of a 0.01 moles/L $NaH_2PO_4$ buffer, having a pH of 7.0, and discarded.

After a purification step with 3 volumes of a 1-mole/L sodium hydroxide solution, the column is washed with WFI and equilibrated once again.

For working up all of the filtered protein solution used, 26 cycles are required, Fractions 1 and 2 in each case being collected in a container. After that, sterile filtration of the separated Fractions 1 and 2 is carried out.

| | |
|---|---|
| Yield, immunoglobulin G in Fraction 2 | 90.3% |
| Yield, albumin in Fraction 1 | 100% |

| Composition of Fractions 1 and 2 in the Capillary Zone Electrophoresis | | |
| --- | --- | --- |
| | Fraction 1 | Fraction 2 |
| Gamma-globulin (%) | 0 | 61.5 |
| β-globulin (%) | 6.1 | 13.5 |
| $\alpha_1$-globulin (%) | 4.3 | 2.1 |
| $\alpha_2$-globulin (%) | 7.7 | 13.3 |
| albumin (%) | 81.9 | 1.8 |
| fibrinogen (%) | 0 | 7.6 |

EXAMPLE 2

The procedure is the same as that of Example 1.

The protein solution, freed from clotting factors, treated with ammonium sulfate and filtered, is chromatographed, as described in Example 1, on a TSK Phenyl 5PW® column.

After Fraction 1 is eluted, the immunoglobulins and lipoproteins are eluted in one fraction from the column with 0.01 moles/L of $NaH_2PO_4$ having a pH of 7.0. The fractions obtained show the following yields:

| Fraction 1: albumin yield | 100% |
| --- | --- |
| Fraction 2: immunoglobulin G yield | 95.5% |

EXAMPLE 3

The procedure is the same as that of Example 1.

The protein solution, freed from clotting factors, treated with ammonium sulfate and filtered, is chromatographed on a 3 L column (180×250 mm), filled with Toyopearl-Phenyl 650M®.

The procedure corresponds to that of Example 1. Per cycle, 2.4 L of the starting solution are processed at a flow rate of 300 mL/min. With this column, three cycles are required for working up 4 L of plasma.

As in Example 1, three fractions are collected.

The fractions obtained show the following yields:

| Fraction 1: albumin yield | 100% |
| --- | --- |
| Fraction 2: immunoglobulin G yield | 96% |

EXAMPLE 4

The procedure is the same as that of Example 1.

The protein solution, freed from clotting factors, treated with ammonium sulfate and filtered, is chromatographed on a 2.5 L column, filled with Toyopearl-Phenyl 650M®.

The procedure corresponds to that of Example 2.

Per cycle, 2.4 L of the starting solution are fractionated a flow rate of 125 mL/min into two fractions. For this purpose, 3 cycles are required.

The fractions obtained show the following yields:

| Fraction 1: albumin yield | 100% |
| --- | --- |
| Fraction 2: immunoglobulin G yield | 95% |

EXAMPLE 5

The procedure of Examples 1, 2, 3 or 4 is followed. Instead of a polyvalent starting plasma, a pre-selected human plasma with a high titer for the cytomegalovirus (anti-CMV) is used and processed as described in Examples 1, 2, 3 or 4.

The fraction 2 obtained therefrom shows the following yields:

| Yield of immunoglobulin G | 90.5% |
| --- | --- |
| Yield of anti-CMV-titer | 78% |

EXAMPLE 6

The procedure of Examples 1, 2, 3 or 4 is followed. Instead of a polyvalent starting plasma, a pre-selected human plasma with a high titer for hepatitis B virus (anti-HBs) is used and processed as in Examples 1 or 2 or 3 or 4.

The fraction 2 obtained therefrom shows the following yields:

| Yield of immunoglobulin G | 92.0% |
| --- | --- |
| Yield of anti-HBs-titer | 82% |

EXAMPLE 7

The procedure of Examples 1, 2, 3 or 4 is followed. Instead of a polyvalent starting plasma, a pre-selected human plasma with a high titer for anti-D is used and processed as in Examples 1 or 2 or 3 or 4.

The fraction 2 obtained therefrom shows the following yields:

| Yield of immunoglobulin G | 91.2% |
| --- | --- |
| Yield of anti-D titer | 54% |

EXAMPLE 8

An immunoglobulin G-containing Fraction 2, prepared as in Example 1, is adjusted by means of ultrafiltration and diafiltration to 0.06 moles/L of $NaH_2PO_4$, a pH of 6.5 and a protein concentration of about 50 g/L. This is followed by a dilution with water for injection purposes (WFI) in the ratio of 1:2. After stirring for 1 hour, the fraction is filtered to clarify and to sterilize it.

A steel column (383 mL), filled with an anion exchanger, such as Poros HQ50®, is equilibrated with a buffer of 0.03 moles/L of $NaH_2PO_4$ having a pH of 6.5.

The conditioned, immunoglobulin G-containing solution (500 mL) is applied to the column at a flow rate of 120 mL/min. The column is washed with 10 volumes of the equilibrated buffer and the immunoglobulin-containing fraction is collected.

The remaining bound proteins are eluted from the column with 0.02 moles/L of $NaH_2PO_4$ and 1.0 moles/L of NaCl at a pH of 6.5. For cleaning the column, the latter is washed with 2 volumes of 1 mole/L of sodium hydroxide and subsequently equilibrated once again.

The total amount of 2.5 L of the starting solution is chromatographed in 5 cycles.

The immunoglobulin G-containing fraction, which is applied and run through, is filtered through a virus filter, such as Planova 35, re-buffered by means of ultrafiltration and diafiltration to 0.02 moles/L of sodium acetate and a pH of 5.5 and adjusted to a protein concentration of about 40 g/L. To this solution, 0.8% (v/v) of octanoic acid is added and, while stirring for 1 hour, the pH is held at 5.5 with 1 moles/L of sodium hydroxide. After that, 0.05 moles of calcium chloride are added, the pH is corrected to a value of 5.5 with 1 mole/L of sodium hydroxide and stirring is continued for 2 hours.

Subsequently, the solution is treated with 2% (w/v) of filter aid, such as standard Super Cell and filtered through a clarifying filter, such as Seitz Supra 80P. The filter cake is washed twice with 100 mL of 0.02 moles/L of sodium acetate having a pH of 5.5.

The filtered solution is treated with 0.3% of TNBP (tri-n-butyl phosphate) and 1% Tween 80 (Polysorbate 80) and stirred for at least 8 hours at room temperature.

At the end of the reaction time, the conductivity is adjusted by dilution with WFI to that of a 0.02 moles/L sodium acetate solution having a pH of 5.0 and the pH is corrected with 10% acetic acid to a value of 5.0.

A steel column (388 mL), filled with an anion exchanger, such as Poros HS50, is equilibrated with a buffer of 0.02 moles/L sodium acetate having a pH of 5.0.

The conditioned immunoglobulin-G solution (2.15 L) is applied to the column at a flow rate of 120 mL/min. The column is washed with 10 volumes of equilibrating buffer, in order to remove the reagents of the octanoic acid and solvent detergent treatment. This washing liquid fraction is discarded.

The bound immunoglobulin G is eluted from the column with 0.02 moles/L of sodium acetate and 0.3 moles/L of sodium chloride at a pH of 5.0 and collected.

The column is cleaned with 0.02 moles/L of sodium acetate and 1.0 mole/L of sodium chloride at a pH of 5.0, followed by 1.0 mole of sodium hydroxide.

After that, the column is equilibrated again. The total amount of 2.3 L of the starting solution is chromatographed in 2 cycles.

By means of ultrafiltration and diafiltration against 0.3 moles/L of glycine having a pH of 5.0, the immunoglobulin G fraction is adjusted to be isotonic, concentrated to a protein content of 50 g/L and filtered to sterilize it.

Yield of immunoglobulin G: 74%

| Analytical Data of a 5% Immunoglobulin G Solution | |
| --- | --- |
| Anti-complementary activity | 0.68 CH$_{50}$/mg of protein |
| Immunoglobulin A | 0.14% |
| Immunoglobulin M | 0.02% |
| Sub-class: | |
| IgG$_1$ | 57.6% |
| IgG$_2$ | 33.3% |
| IgG$_3$ | 5.5% |
| IgG$_4$ | 3.6% |
| cellulose acetate electrophoresis | 100% gamma-globulin |
| pre-kallikrein activator | neg. |
| pre-kallikrein | neg. |
| kallikrein | neg. |
| kininogen | neg. |

| -continued | |
| --- | --- |
| Analytical Data of a 5% Immunoglobulin G Solution | |
| plasmin | neg. |
| plasminogen | neg. |
| Factor XI | neg. |

Figure 5:
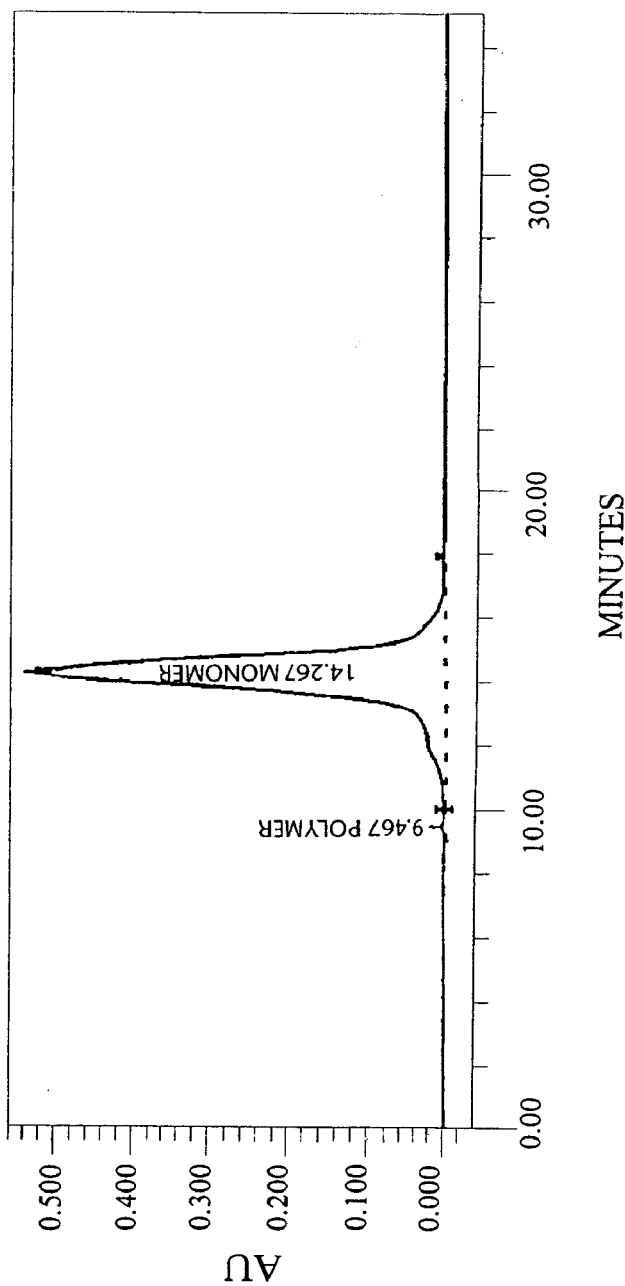

The HPSE chromatogram is given in FIG. 5

EXAMPLE 9

An albumin-containing Fraction 1, prepared as in Example 1, is adjusted by means of ultrafiltration and diafiltration to 0.02 moles/L of NaH$_2$PO$_4$ and 0.15 moles/L of sodium chloride having a pH of 7.0.

A 50 mL column (1.5×25 cm), filled with AF-Heparin Toyopearl®, is equilibrated with 0.02 moles/L of NaH$_2$PO$_4$ and 0.150 moles/L of sodium chloride having a pH of 7.0.

The albumin-containing fraction (100 mL) is applied at a flow rate of 7 mL/min to the column. The column is rinsed with 5 volumes of the equilibration buffer and this albumin-containing fraction is collected.

The column is washed with 0.02 moles/L of NaH$_2$PO$_4$ and 0.4 moles/L of NaCl having a pH of 7.0 and this fraction is discarded. The AT-III is eluted with a buffer consisting of 0.02 moles/L of NaH$_2$PO$_4$ and 2.0 moles/L of sodium chloride having a pH of 7.0. This fraction is re-buffered by means of ultrafiltration/diafiltration to PBS, concentrated and sterilized.

The analytical date of the AT-III solution obtained is as follows:

| | |
| --- | --- |
| AT-III yield | 91% |
| protein | 1.1 g/L |
| AT-III activity | 805% d.N. |
| AT-III antigen | 1.0 g/L |
| albumin | <0.006 g/L |

Figure 6:
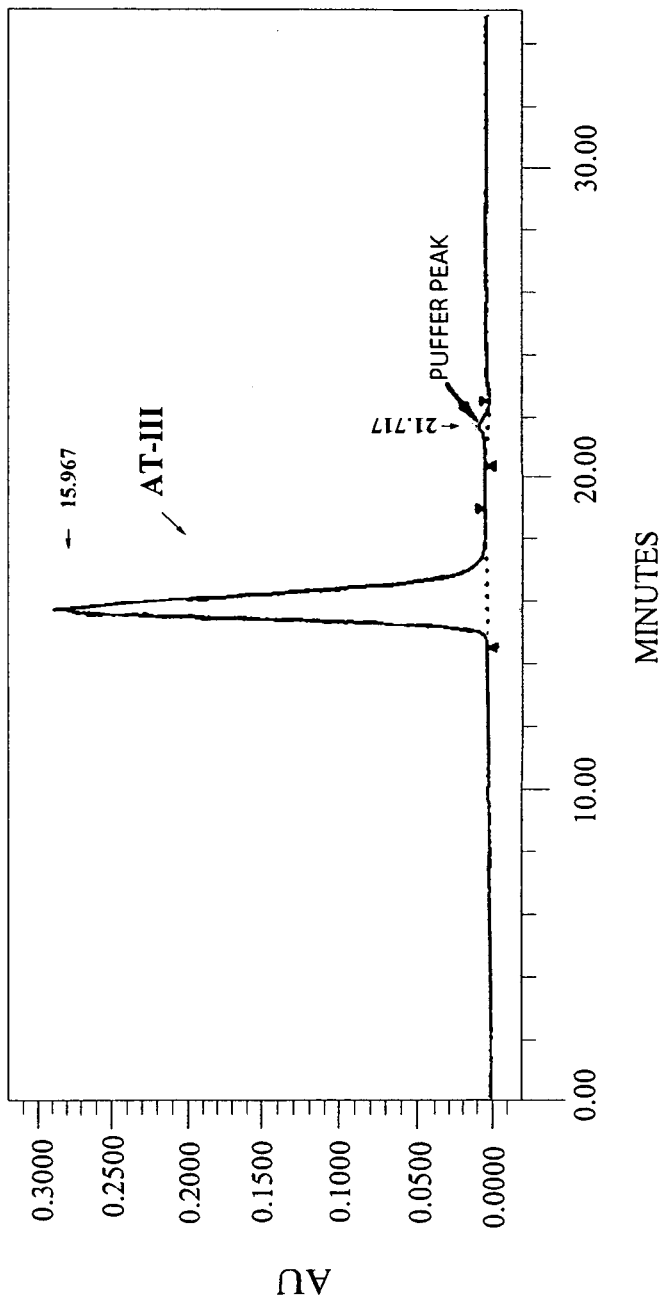

The HPSE chromatogram is given in FIG. 6.

TABLE 1

Determination of the Ammonium Sulfate Concentration for the Hydrophobic Interaction Chromatography

| | Protein (g/L) | IgG (g/L) | IgA (g/L) | IgM (g/L) | Albumin (g/L) |
| --- | --- | --- | --- | --- | --- |
| Starting point | 26.7 | 3.59 | 0.78 | 0.34 | 15.8 |
| 0.5 moles ammonium sulfate | 26.7 | 3.59 | 0.78 | 0.34 | 15.8 |
| 0.7 moles ammonium sulfate | 26.7 | 3.59 | 0.78 | 0.34 | 15.8 |
| 0.8 moles ammonium sulfate | 26.7 | 3.59 | 0.78 | 0.34 | 15.8 |
| 1.0 mole ammonium sulfate | 26.0 | 3.40 | 0.72 | 0.35 | 14.8 |
| 1.2 moles ammonium sulfate | 24.9 | 1.93 | 0.38 | 0.21 | 15.7 |
| 1.4 moles ammonium sulfate | 22.0 | 0.73 | 0.16 | 0.10 | 14.4 |

TABLE 2

Example of an Inventive Hydrophobic Interaction Chromatography of Human Plasma at Different Ammonium Sulfate Concentrations

|  | 0.7 Moles | 0.8 Moles | 1.0 Moles |
|---|---|---|---|
| Starting point Albumin (%) | 100 | 100 | 93.7* |
| IgG (%) | 100 | 100 | 94.7* |
| Fraction 1 Albumin (%) | >95.0 | >95.0 | >95.0 |
| IgG (%) | 34.4 | <2.6 | <2.0 |
| Fraction 2 Albumin (%) | 1.4 | 1.8 | 3.3 |
| IgG (%) | 57.2 | >95.0 | >95.0 |

*Precipitation by ammonium sulfate

TABLE 3

Distribution of Relevant Plasma Protein in Fractions of Hydrophobic Interaction Chromatography

|  | Starting point (%) | Fraction 1 (%) | Fraction 2 (%) |
|---|---|---|---|
| IgG | 100 | <5 | >90 |
| IgA | 100 | <2 | >95 |
| IgM | 100 | <5 | >90 |
| Albumin | 100 | >95 | <2 |
| Transferrin | 100 | >95 | <2 |
| AT-III | 100 | >90 | <10 |
| $\alpha_1$-anti-trypsin | 100 | >90 | <5 |
| Lipids/lipoproteins | 100 | <5 | >70 |

Caption for FIG. 5:

HPSE Chromatogram of an Immunoglobulin G Solution, Prepared According to Example 8

Caption for FIG. 6:

HPSE Chromatogram of an Antithrombin (AT-III) Solution, Produced by Example 8

What is claimed is:

1. A method for fractionating plasma or serum, said method comprising subjecting a starting solution, containing plasma or serum, to a fractionation by hydrophobic interaction chromatography without rivanol precipitation, wherein during said hydrophobic interaction chromatography a stepwise salt gradient is employed to obtain (at least) one immunoglobulin-containing fraction and one albumin-containing fraction.

2. The method of claim 1, wherein the starting solution contains a plasma or serum of human origin.

3. The method of claim 2, wherein the starting solution contains polyvalent human plasma.

4. The method of claim 2, wherein the starting solution contains selected human plasma, selected with respect to viral, bacterial or antibodies, directed against cellular antigens.

5. The method of claim 1, wherein an ammonium sulfate gradient is used for the chromatography.

6. The method of claim 5, wherein the chromatography comprises a first fractionation step at a high concentration of ammonium sulfate, and a second fractionation step at a lower concentration of ammonium sulfate.

7. The method of claim 6, wherein the high concentration of ammonium sulfate is between 0.6 and not more than 1.4 moles/L and the lower concentration is between 0 and 0.4 moles/L.

8. The method of claim 6, wherein the high concentration of ammonium sulfate is 0.7 to 1 moles/L, and the lower concentration is between 0 to 0.3 moles/L.

9. The method of claim 1, wherein the starting solution and the chromatography solid phase are adjusted to a desired high salt-gradient concentration at the start of the fractionation.

10. The method of claim 1, wherein the starting solution contains plasma, from which the clotting factors of the PPSB complex have been removed.

11. The method of claim 1, wherein the starting solution contains plasma or serum from which clotting factor VIII has been removed.

12. The method of claim 1, wherein, after obtaining a first fraction, two further fractions are obtained by means of step gradients.

13. The method of claim 12, wherein, after the first fraction, the fractionation commences with an ammonium sulfate buffer having a concentration of 0.4 to 0.1 moles/L, which is then lowered to less than 0.1 to 0 moles/L.

14. The method of claim 1, wherein phenyl-substituted or alkyl-substituted phases, based on copolymers of glycidyl methacrylate and ethylene glycol dimethacrylate, copolymers of polystyrene or divinylbenzene or silica, coated with dextran or polymers, are used as hydrophobic interaction solid phase.

15. The method of claim 14, wherein copolymers of glycidyl methacrylate and ethylene glycol dimethacrylate are used as hydrophobic interaction solid phase.

16. The method of claim 14, wherein the fractionation employs a high concentration of ammonium sulfate buffer of 0.8 to 1.0 moles/L and a lowered concentration of ammonium sulfate of 0.3 to 0 moles/L.

17. The method of claim 16, wherein a first fraction is obtained at an ammonium sulfate concentration of 0.9 moles/L and, after that, a step gradient is employed, the ammonium sulfate concentration initially being 0.3 moles/L and then lowered to 0 moles/L.

18. The method of claim 1, wherein a first fraction obtained is worked up and therapeutically usable antithrombin III, transferrin and/or albumin are obtained.

19. The method of claim 18, wherein the first fraction obtained is worked up by affinity chromatography followed by anion exchange chromatography and virus inactivation as well as filtering, concentrating and sterilizing steps.

20. The method of claim 1, wherein a second faction obtained is worked up and therapeutically usable immunoglobulin is obtained.

21. The method of claim 20, wherein the second fraction obtained is worked up by anion exchanger chromatography, virus inactivation, octanoic acid treatment, as well as cation exchanger chromatography and filtering, sterilizing and concentrating steps into a compatible immunoglobulin G preparation.

22. The method of claim 20, wherein the therapeutically usable immunoglobulin is IgG.

23. A therapeutic method comprising the following steps:
a) carrying out the method of claim 1 to obtain a therapeutically usable immunoglobulin preparation, an antithrombin III preparation, an albumin preparation or a transferrin preparation; and
b) administering a therapeutically effective amount of at least one of said preparation to a patient in need thereof.

* * * * *